United States Patent
Potyrailo et al.

(10) Patent No.: US 8,364,419 B2
(45) Date of Patent: Jan. 29, 2013

(54) SENSOR SYSTEM AND METHODS FOR SELECTIVE ANALYTE DETECTION USING RESONANCE SENSOR CIRCUIT

(75) Inventors: Radislav Alexandrovich Potyrailo, Niskayuna, NY (US); James Anthony Cella, Clifton Park, NY (US); Cheryl Margaret Surman, Albany, NY (US); Kelly Scott Chichak, Clifton Park, NY (US); Steven Go, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 492 days.

(21) Appl. No.: 12/424,016

(22) Filed: Apr. 15, 2009

(65) Prior Publication Data
US 2010/0268479 A1    Oct. 21, 2010

(51) Int. Cl.
*G01N 31/00*    (2006.01)
(52) U.S. Cl. .......................................................... 702/24
(58) Field of Classification Search .................... 702/24, 702/23, 25, 27, 30, 32
See application file for complete search history.

(56) References Cited

U.S. PATENT DOCUMENTS

| | | | |
|---|---|---|---|
| 6,773,926 B1 * | 8/2004 | Freund et al. ................. | 436/149 |
| 7,126,013 B2 | 10/2006 | Heeney et al. | |
| 7,335,336 B1 * | 2/2008 | Kim ............................... | 422/88 |
| 2007/0029195 A1 | 2/2007 | Li et al. | |
| 2007/0090926 A1 * | 4/2007 | Potyrailo et al. ........... | 340/10.41 |
| 2008/0012577 A1 * | 1/2008 | Potyrailo et al. .............. | 324/633 |
| 2008/0116908 A1 * | 5/2008 | Potyrailo et al. .............. | 324/721 |
| 2009/0278685 A1 * | 11/2009 | Potyrailo et al. ........... | 340/572.1 |
| 2012/0235690 A1 * | 9/2012 | Potyrailo et al. .............. | 324/652 |

OTHER PUBLICATIONS

Richard D Yang, Bernd Fruhberger, Jeongwon Park and Andrew C. Kummel; "Chemical identification using an impedance sensor based on dispersive charge transport"; Appl. Phys. Lett. 88, 074104 (2006); DOI:10.1063/1.2175491; Published Feb. 17, 2006; accepted Jan. 3, 2006; published Feb. 17, 2006; Abstract 3pages.

M.E.H.Amrani and P.A.Payne; "Multi-frequency interrogation technique applied to conducting polymer gas and odour sensors"; IEE Proc.-Sci. Meas. Technol., vol. 144, No. 2, Mar. 1999; DOL 10.1049/ip-smt:19990288; 7pages.

Hua Bai and Gaoquan Shi; "Gas Sensors Based on Conducting Polymers"; / Accepted: Mar. 2, 2007 / Published: Mar. 7, 2007; Sensors 2007, 7, 267-307.

Jiri Janata and Mira Josowicz; "Conducting polymers in electronic chemical sensors"; School of Chemistry and Biochemistry,Georgia Institute of Technology,Atlanta,Georgia 30332-0400,USA; e-mail: jiri.janata@chemistry.gatech.edu.; nature materials | vol. 2 | Jan. 2003 | www.nature.com/naturematerials; 6pages.

S. W. Thomas and T. M. Swager; "Conjugated Polymer Sensors: Design Principles Towards Enhanced Versatility"; Report Number: A035334; Report Date: Dec. 2004; Abstract 2pages.

* cited by examiner

*Primary Examiner* — Cindy H Khuu
(74) *Attorney, Agent, or Firm* — Jenifer E. Haeckl (57) ABSTRACT

A system, device and methods, for determining at least two analytes, wherein the system and device include at least one resonant sensor circuit that includes a sensing material that predictably affects the resonant complex impedance response of a sensor electrode. The sensing material has at least two material properties that change when the materials are exposed to two or more analytes. The system and device also include a processor that generates a multivariate sensor response pattern that is based at least in part on a change in the two material properties of the sensing material.

25 Claims, 12 Drawing Sheets

SENSOR SYSTEM AND METHODS FOR SELECTIVE ANALYTE DETECTION USING RESONANCE SENSOR CIRCUIT

BACKGROUND

The invention relates to sensors and methods for analyte detection, and more particularly to sensors and methods for chemical and biological sensing applications.

An appropriate selection of sensing material is one of the aspects in sensor performance and application. The key performance indicators for sensors are selectivity, sensitivity and reliability.

Selectivity is the ability of the sensor to respond only to a specific analyte or a group of analytes. High sensor selectivity is required to detect trace concentrations of analytes in the presence of other contaminants, which result in high background levels of interference. Currently known sensors do not exhibit high selectivity under such conditions.

Sensitivity of a sensor is the output produced per unit change in concentration of an analyte. Stability of the sensor sensitivity and selectivity are also important factors. This stability of sensitivity and selectivity of the sensor is known as reliability.

Impedance spectroscopy is a standard technique currently used to characterize fundamental aspects of material performance. In impedance spectroscopy, a sensing material is positioned between electrodes and is probed over a wide frequency range (from a fraction of Hz to tens of MHz) to extract the fundamental information about dielectric properties of the material and vapor effects on these properties. But applicability of impedance spectroscopy in practical sensors for detection of trace levels of analytes is limited due to its low sensitivity in reported measurement configurations and prohibitively long acquisition times over the broad frequency range.

Therefore, there is a need for sensing materials in combination with a proper transducer to achieve high levels of sensitivity, selectivity and reliability for identifying analytes.

BRIEF DESCRIPTION

In one embodiment, a system for selectively determining at least two analytes, comprising at least one resonant sensor circuit comprising a sensing material that predictably affects the resonant complex impedance response of a sensor electrode, wherein the sensing material comprises at least two material properties that change upon exposure to two or more analytes and a processor that generates a multivariate sensor response pattern that is based at least in part on a change in the two material properties of the sensing material.

In another embodiment, a system for selectively determining at least two analytes, comprising at least one resonant sensor circuit comprising a sensing material that predictably affects the resonant complex impedance response of a sensor electrode structure wherein the sensor electrode structure comprises an inductor-capacitor-resistor circuit and wherein the sensing material comprises at least two material properties that change upon exposure to two or more analytes and a processor that generates a multivariate sensor response pattern that is based at least in part on a change in the two material properties of the sensing material.

In yet another embodiment, a sensing device adapted to detect at least two analytes, comprising a resonant sensor circuit comprising a sensor electrode and a sensing material disposed on the sensor electrode, wherein the sensing material comprises at least two material properties that change upon exposure to two or more analytes; a processor that generates a multivariate sensor response pattern that is based at least in part on a change in the two material properties of the sensing material and a memory chip storing user-defined digital data.

In one embodiment, a method for selectively detecting at least two or more analytes in presence of an interference, comprising contacting a sensor with an analyte; wherein the sensor comprises at least one resonant sensor circuit comprising a sensing material comprises at least two material properties that change in the presence of two analytes; and generating a multi-variate sensor response pattern.

DRAWINGS

These and other features, aspects, and advantages of the present invention will become better understood when the following detailed description is read with reference to the accompanying drawings in which like characters represent like parts throughout the drawings, wherein.

These and other features, aspects, and advantages of the present invention will become better understood when the following detailed description is read with reference to the accompanying drawings in which like characters represent like parts throughout the drawings, wherein.

DETAILED DESCRIPTION

Figure 7A:
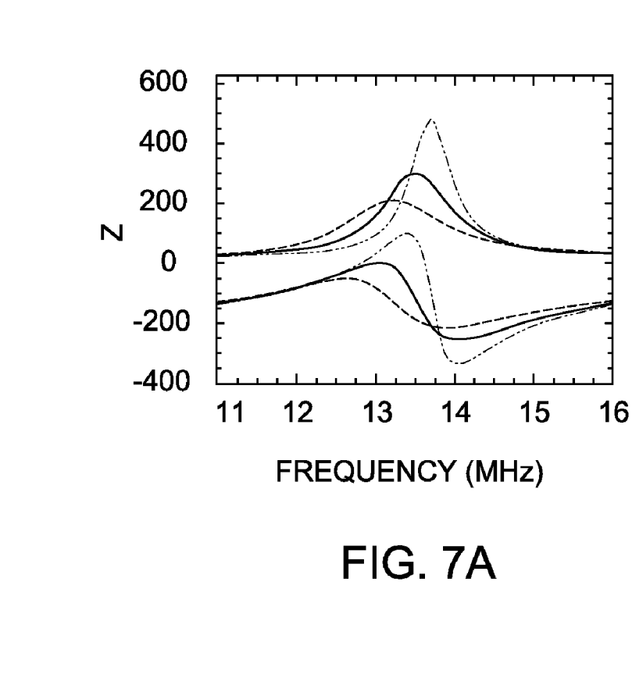
FIG. 7 is a schematic presentation of resonant complex impedance spectra of three vapors obtained using a multi-variate sensor and conversion of these resonant complex impedance spectra using principal components analysis (PCA) to a response pattern of three different vapors.
Figure 7B:
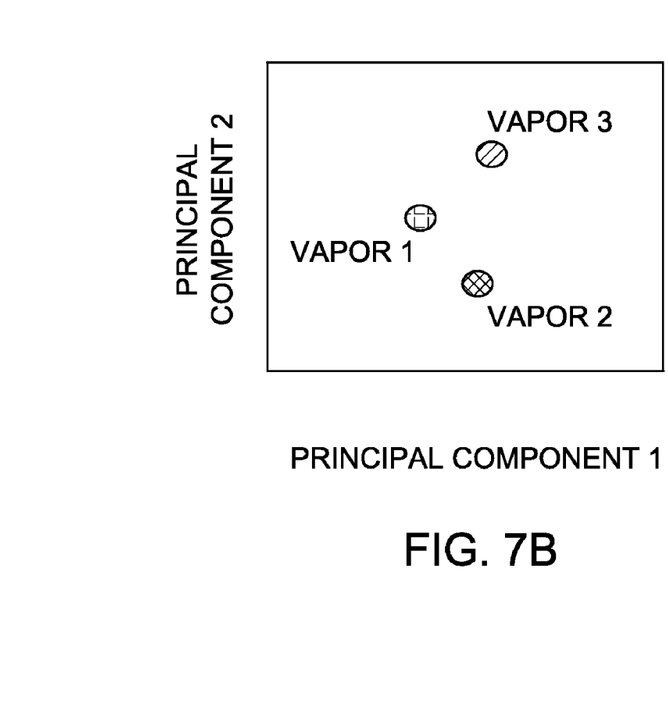
Figure 8A:
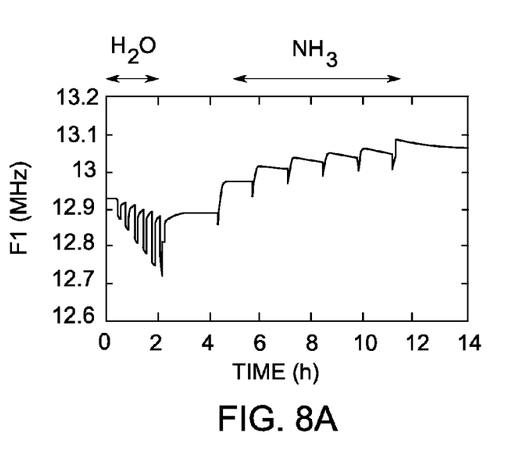
FIG. 8 is a selective analysis of $NH_3$ and $H_2O$ vapors using a single resonant multi-variate sensor. (A-D) Sensor responses $F_1$, $F_2$, $F_p$, and $Z_p$, respectively upon exposures of sensor to $H_2O$ vapor (630, 1260, 2205, 3150, 4410, and 6300 ppm) and to $NH_3$ vapor (4, 8, 14, 20, 8, and 40 ppm).
Figure 8B:
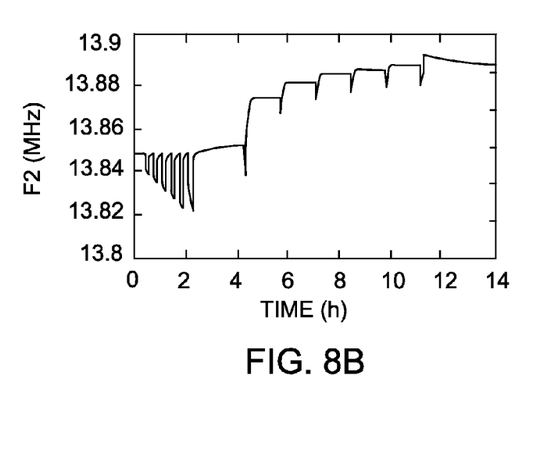
Figure 8C:
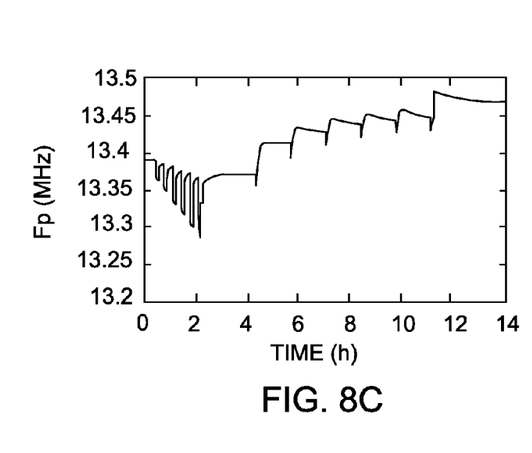
Figure 8D:
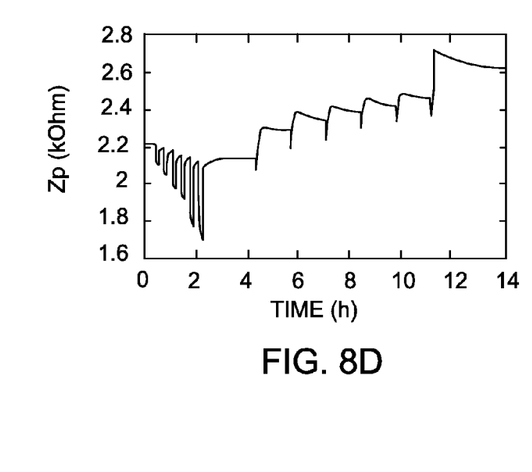

The term 'multi-variate sensor' is referred to herein as a single sensor that produces multiple response signals that are not substantially correlated with each other and where these individual response signals from the multi-variate sensor are further analyzed using multivariate analysis tools to construct response patterns of exposures to different analytes and their different concentrations. In one embodiment, multivariable or multivariate signal transduction is performed on the multiple response signals using multivariate analysis tools to construct a multivariate sensor response pattern. The response pattern of a sensor using multivariable signal transduction is shown in FIG. 7, which will be discussed in detail later in the description.

The term 'predictably affects' with respect to sensor operation is referred to herein, as when a calibration function of the sensor exists that relates the sensor response to analyte concentration through a mathematical function where one sensor multivariate output corresponds to one analyte concentration. The sensor response is predictably affected by the analyte when the calibration function of the sensor is used to calculate the analyte concentration from the sensor response.

One or more embodiments of the sensor system generally comprise at least one resonant sensor circuit comprising a sensing material having at least two material properties that change at different ratios in the presence of different analytes. In one embodiment, the sensor circuit is configured to detect more than one analyte using at least two vapor response mechanisms of a sensing material and where the sensing material has at least two material properties that change upon exposure to one or more analytes. The sensor generates a multi-variate response pattern upon sensor exposure to different analytes. The sensor may comprise resonant electronic circuits and/or resonant optical circuits.

Figure 1:
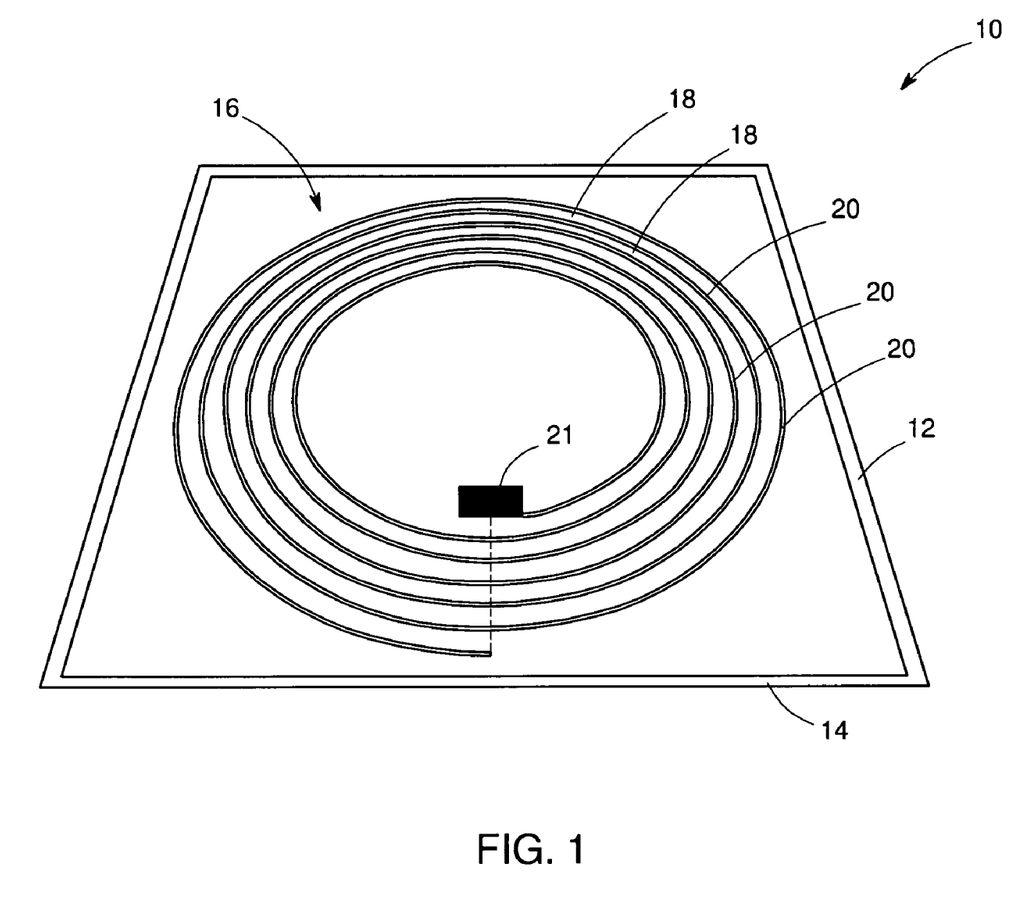
FIG. 1 is a top view of an embodiment of a radio frequency based sensor of the invention.
Figure 2:
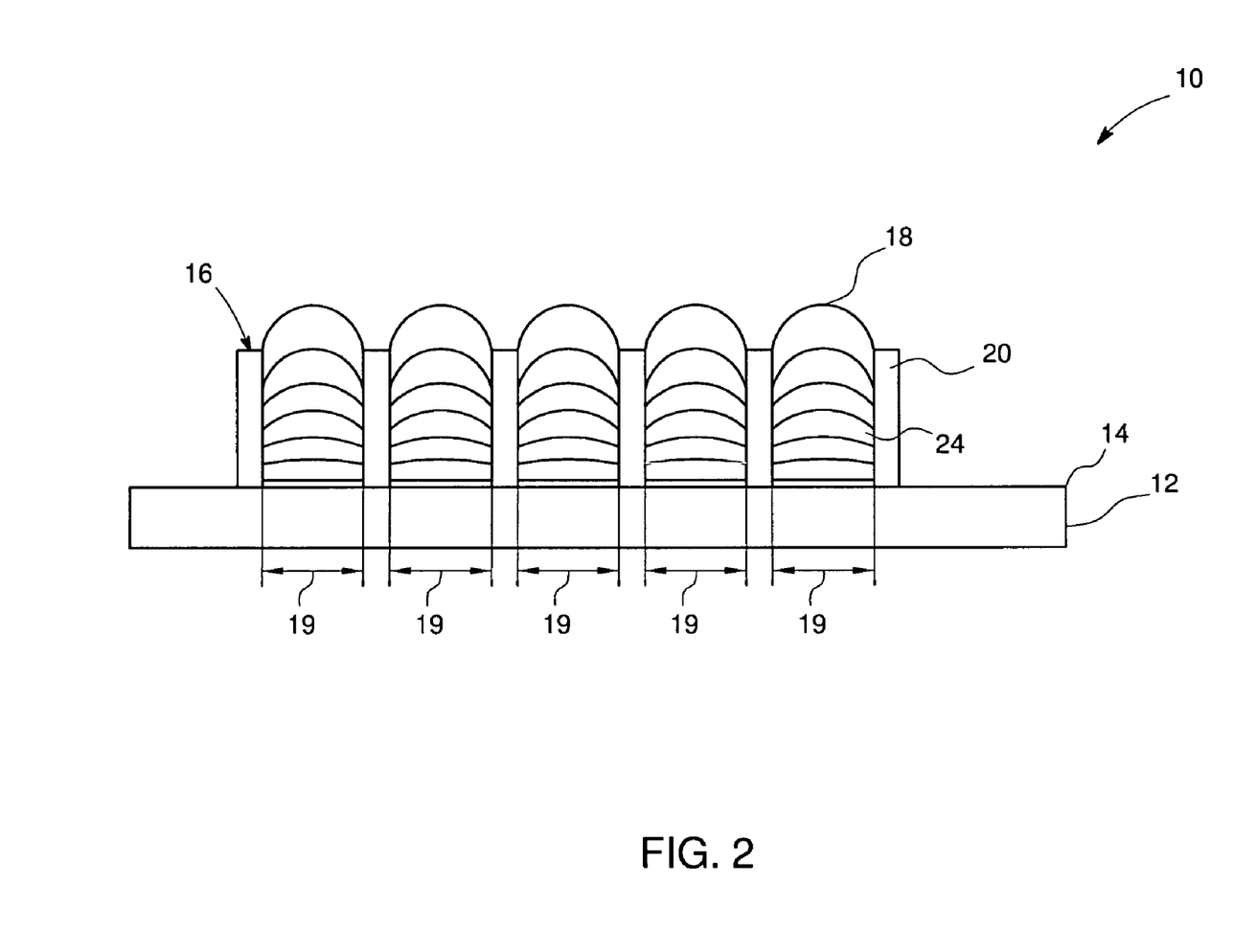
FIG. 2 is a cross-sectional view of a portion of the radio frequency based sensor of FIG. 1, wherein the sensing material is disposed between the concentric electrodes.
Figure 3:
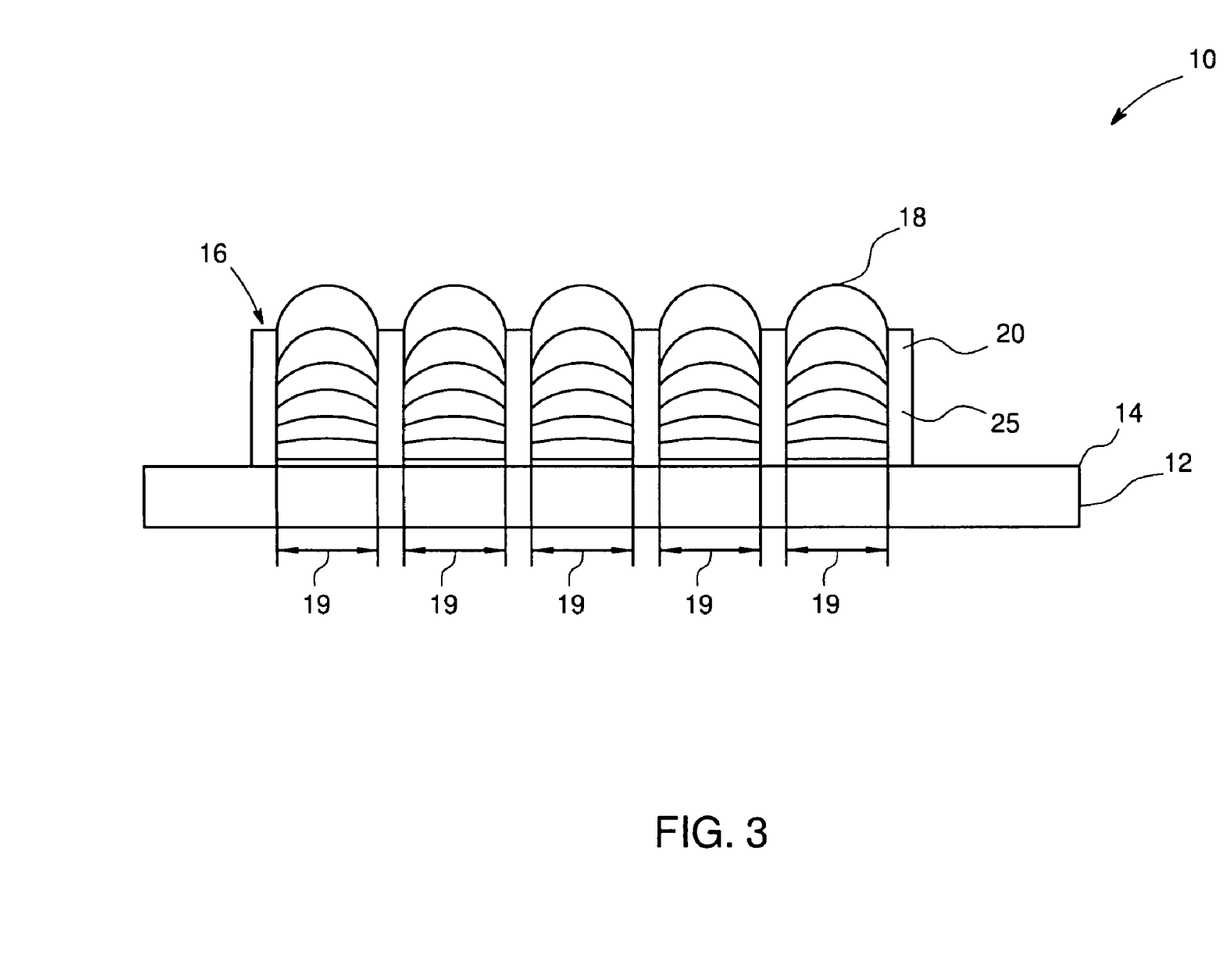
FIG. 3 is a cross-sectional view of another embodiment of a radio frequency based sensor wherein the sensing material is disposed as a coating on the concentric electrodes.
Figure 4:
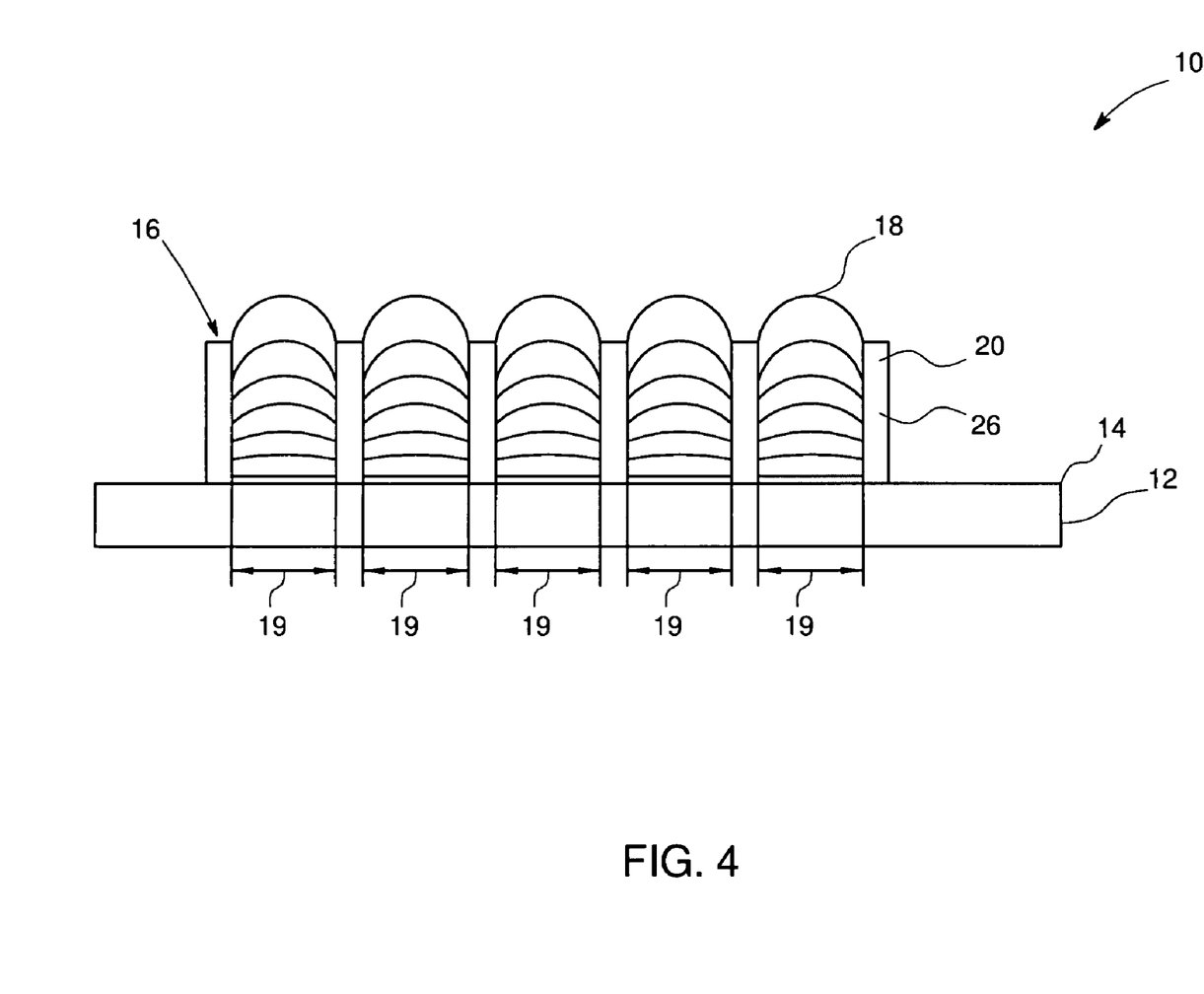
FIG. 4 is a cross-sectional view of a portion of the radio frequency based sensor of FIG. 1, wherein the sensing material is disposed between and on the concentric electrodes.

An embodiment of the sensor system is generally shown and referred to in FIGS. 1 2 and 3 as sensor 10, and comprises a radio frequency identification (RFID) device. The sensor 10 comprises a resonance frequency sensor circuit employing a radio frequency tag 12 having a substrate 14, an antenna 16, and a memory chip 21. Antenna 16 is formed as a coil with essentially concentric electrodes 20 that form a coil. The memory chip 21 is used to store data information. Nonlimiting examples of such data are information on the detected analyte, calibration parameters of the sensor, user defined information (manufacturing date, expiration date), authentication data. The radio frequency tag 12 induces an associated electromagnetic field 18 formed between electrodes 20. The space between electrodes 20 forms sensing regions 19. Sensing materials 24 may be present in the sensing regions 19 and may be in operative association with the substrate 14. The sensing materials 24 are capable of interacting or binding to a target analyte. In one embodiment, the sensing materials are placed in the electromagnetic field of the electrodes. In the embodiment of FIG. 2, the sensing materials 24 are disposed between the pairs of electrodes 20 in the sensing regions 19. In another embodiment, as illustrated in FIG. 3, the sensing materials 25 are disposed as a coating on the electrodes. In some embodiments, the sensing material is at least partially in contact with one of the electrodes and in other embodiments the sensing material 26 is in contact with all electrodes (FIG. 4).

Figure 5:
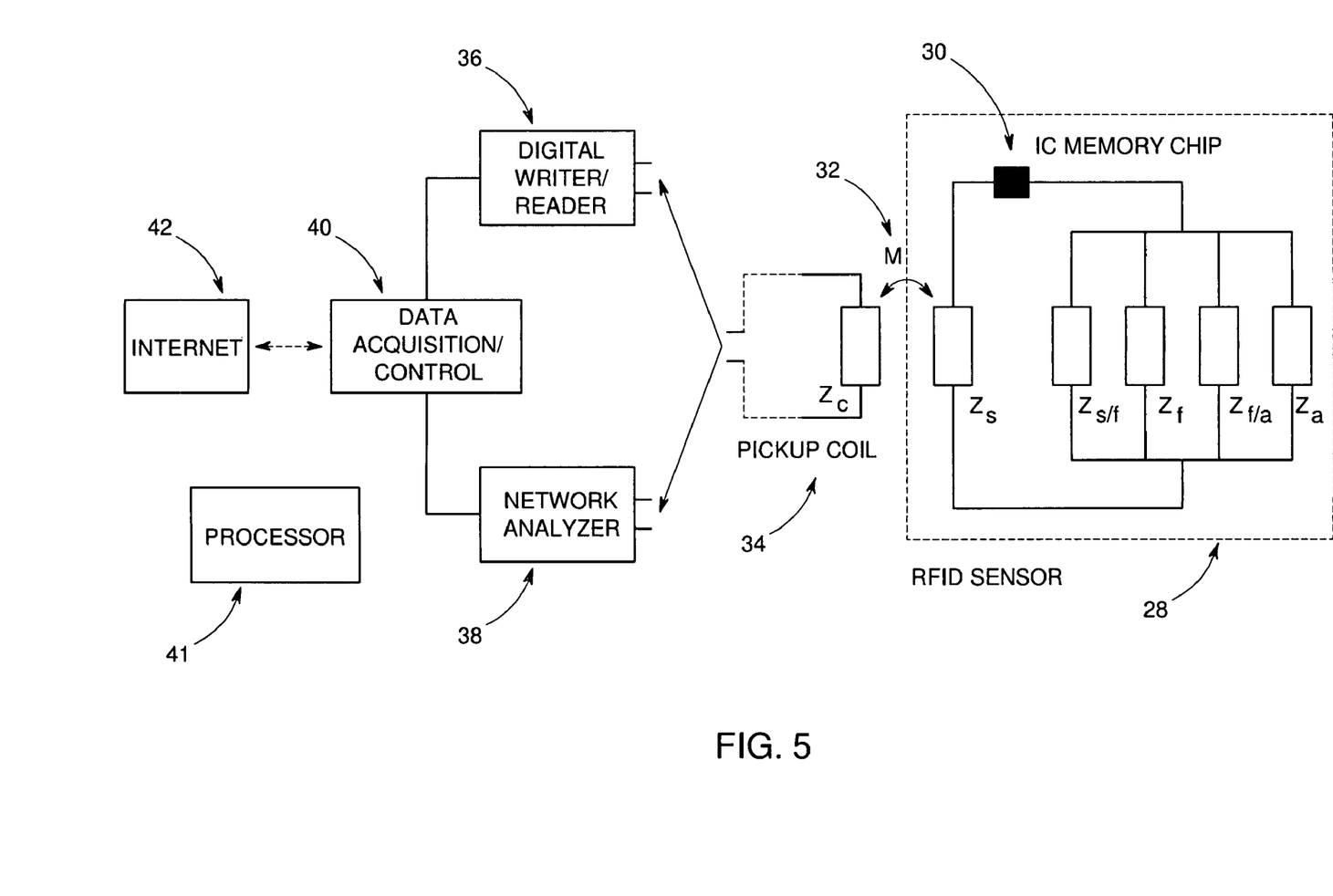
FIG. 5 is a schematic representation of operation of one of the disclosed multi-variate sensors, nonlimiting example.

In some embodiments, the system or the sensor system comprises an inductor-capacitor-resistor (LCR) circuit with a resonance frequency response provided by the complex impedance (Z) of this circuit. In the most general description, four quantities, such as resistance (R), capacitance (C), inductance (L) and frequency (f), determine the complex impedance (Z) of a circuit or a circuit part. In general, the multi-variate sensor has a complex impedance that includes a complex impedance of the sensor electrode structure $Z_s$, complex impedance of the sensing film $Z_f$, complex impedance of the interface between the sensor electrode structure and the sensing film $Z_{s/f}$, complex impedance of the interface between the sensing film and the analyzed fluid $Z_{f/a}$, and complex impedance of the analyzed fluid $Z_a$. The relation between $Z_s$, $Z_f$, $Z_{s/f}$, $Z_{f/a}$, and $Z_a$ is that they are as series or parallel circuits. In a non-limiting example, FIG. 5 illustrates that $Z_f$, $Z_{s/f}$, $Z_{f/a}$, and $Z_a$ are in parallel, while their combination is in series with $Z_s$ and the integrated circuit (IC) memory chip (30). The RFID sensor (28) comprises $Z_s$, $Z_f$, $Z_{s/f}$, $Z_{f/a}$, and $Z_a$ and is being interrogated with a pick up coil (34) of the sensor reader. The pick up coil has its complex impedance of the pick up coil $Z_c$. The coupling between the pick up coil and the sensor is performed through a mutual inductance coupling M (32). The total complex impedance of the sensor is measured using a network analyzer (38), while the digital information from the memory chip is measured with a digital writer/reader (36). These measurements are performed, for example, using a multiplexer. In a non-limiting example, the data acquisition and control (40) is further accomplished and data is sent via Internet (42) to an end-user. In some embodiments, a processor 41 is present in the system to generate a multivariate sensor response pattern that is based at least in part on a change in the two material properties of the sensing material. In some embodiments, a processor (41) is present in addition to the data acquisition and control 40. For example, the processor 41 may acquire the sensor and calibration data from the data acquisition and control (40) to generate the multivariate sensor response pattern, which may subsequently be sent to the end user via the Internet. Alternatively, the processor 41 may be present at the user end, and receives raw or semi-processed data through the Internet and generates the multivariate sensor response pattern.

The sensor system can also operate with or without the memory chip. The sensor system can operate over different frequency ranges where the interrogation of the sensor system can be performed using different methods known in the art with non-limiting examples of measurements in the kilo-Hertz, Mega-Hertz, Giga-Hertz, Tera-Hertz, infrared, visible, and ultraviolet range of electromagnetic frequency spectrum. In some embodiments, the sensor system operates within an electro magnetic spectrum comprises a frequency range from about 105 Hertz to 1015 Hertz. Sensor system can be wireless or wired to a sensor reader. The total complex impedance of the sensor system is measured using any known measurement technique with nonlimiting examples that include frequency scanning and sensor excitation with a pulsed signal to observe the sensor ring-time. Further, depending on the particular measurement application and particular sensor design, relative contributions of Zs, Zf, Zs/f, Zf/a, and Za may vary. The type of a sensing material affects the complex impedance of the sensing film Zf. The type of a sensing material and the method of application of the sensing material onto the electrode structure of the sensor system affect the complex impedance of the interface between the sensor electrode structure and the sensing film Zs/f. The type of a sensing material, the method of application of the sensing material onto the electrode structure of the sensor system, and the morphology of the sensing material affect the complex impedance of the interface between the sensing film and the analyzed fluid Zf/a. The type of analyzed fluid sample (liquid or gas) affects the complex impedance of the analyzed fluid Za. In some embodiments, a processor is present in the system to generate a multivariate sensor response pattern that is based at least in part on a change in the two material properties of the sensing material.

Figure 6:
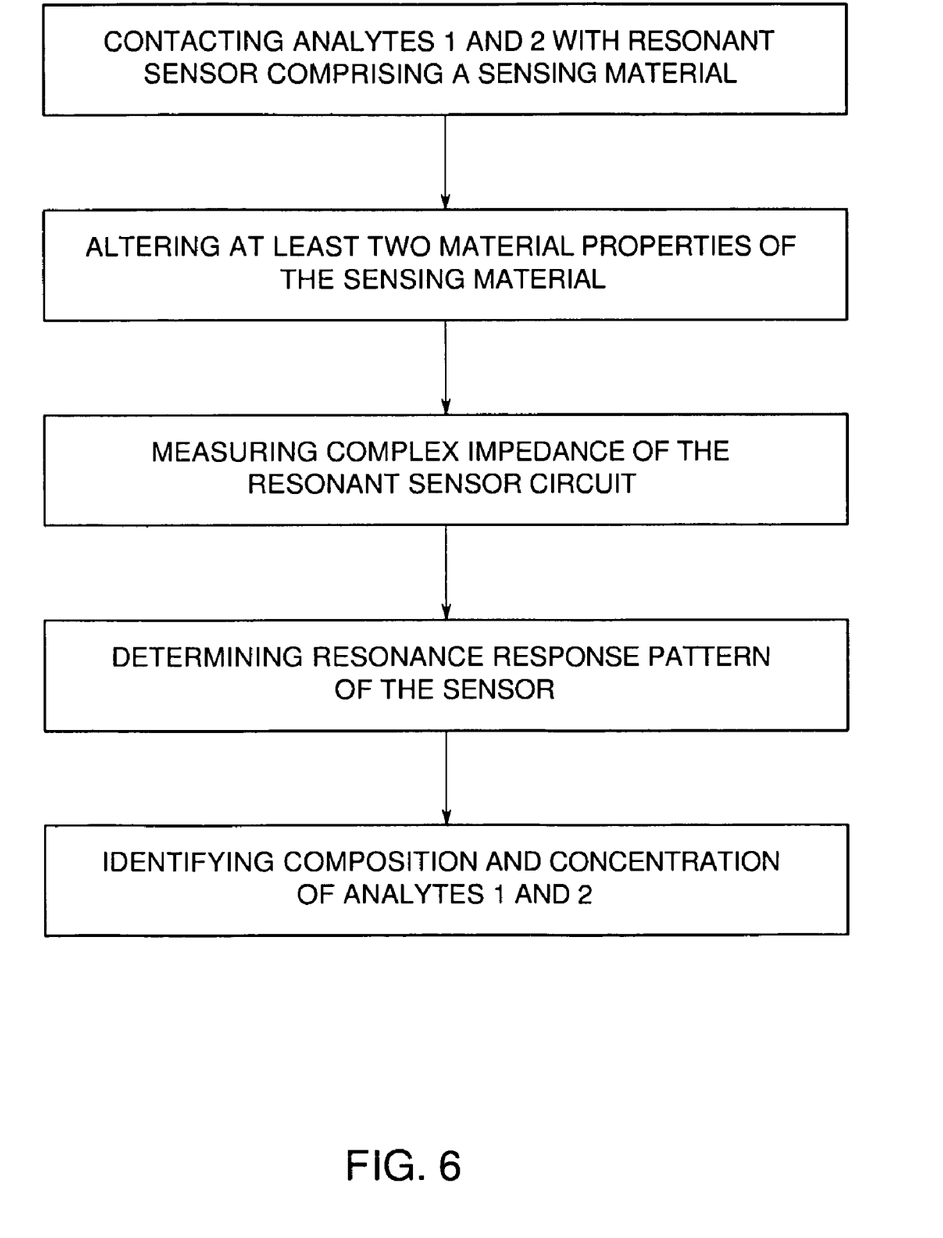
FIG. 6 is a method for selective detection of at least two analytes with one multi-variate sensor.

In one embodiment, a method for selective detection of at least two analytes with one multi-variate sensor system is described (FIG. 6). The method comprises the steps of contacting at least two analytes with a resonant sensor, wherein the sensor system comprises at least one resonant sensor circuit and altering at least two sensing material properties followed by measuring complex impedance response of the resonant sensor circuit, and determining a multivariate response pattern of the sensor system by performing a multivariate analysis of the complex impedance response. Finally, from this pattern, the sensor system identifies the analytes and concentrations of at least two analytes. One of analytes may be the analyte of interest to the end-user while the second analyte may be not of interest to the end-user (an interferent) or may be another analyte also of interest to the end-user.

In certain embodiments, the electrode material may be adapted to transport electrical current with determined electrical properties. Non-limiting examples of electrode materials include metals such as copper, aluminium, gold, silver, alloys of copper (e.g. brasses, bronzes), alloys of aluminum (e.g. NAMBE™ which is an alloy of aluminium and seven other non-specified metals, and SILUMIN™ alloy of aluminium and silicon), alloys of gold (e.g. ELECTRUM™ which is an alloy of gold and silver, with trace amount of copper and other metals), conducting polymers, doped conducting polymers, such as doped polyacetylene, doped polyaniline, doped polythiophene, carbon nanotubes, carbon fibers, carbon particles, carbon paste, conducting inks, or combinations thereof. In certain embodiments, the electrode material is inert to analytes. In certain embodiments, the electrode material may also provide a function of a sensing material, when, for example, electrode material is a conducting polymer, doped conducting polymer and any other material that will predictably affects sensor response.

In various embodiments, the system may include an antenna having less than one turn, one turn or more than one turn. Such an antenna may be fabricated by employing techniques, such as, but not limited to, microlithography, nanolithography, screen-printing. The resonance sensor circuit may include additional elements such as, but not limited to, integrated circuit memory chip and capacitors. In one embodiment, the sensor system comprises a processor to generate a multivariate sensor response pattern that is based at least in part on a change in the two material properties of the sensing material.

In some embodiments, the sensing materials are applied onto a resonant sensor to induce changes in the resonant complex impedance of the sensor. The sensors use changes such as, but not limited to, dielectric, dimensional, and charge transfer, physical sorption, chemical sorption, Schottky barrier interfacial potential, electronic donation, hydrogen bonding, charge-trapping changes of sensor material properties to induce changes in resonant properties of the resonant circuit.

Non-limiting examples of analytes that may be detected by embodiments of the sensors system of the present invention include inorganic gases, volatile organic compounds (VOC), oxidizing and reducing gases, dissolved gases, biological species in water or in air or combinations thereof.

The radio frequency based sensors of the invention, may be employed in a detection system. For example, the detection system may comprise a sample delivery unit for delivering a sample to the radio frequency based sensor, and a display device, such as a monitor, for displaying the electrical signal representative of a binding event.

The sensor may be wireless, or wired, or electronic, (radio frequency identification) RFID based, non-RFID based, or combinations of two or more. In embodiments where the sensor is a RFID based sensor, the sensor may be a wireless sensor. Also, the RFID based sensor may include a passive RFID tag, or a semi-passive RFID tag, or an active RFID tag. Further, the RFID tags may be configured to operate at frequencies ranges, such as but not limited to, low frequency range from about 125 KHz to about 135 KHz, high frequency range of about 13.56 MHz, ultra high frequency (UHF) range from about 850 MHz to about 960 MHz, and microwave frequency range of about 2.45 GHz-5.8 GHz.

In one embodiment, non limiting examples of sensing material comprises carbon nanotubes, metal oxide nanotubes, semiconducting nanotubes, mixture of semiconducting and metallic nanotubes, graphene, functionalized nanotubes, functionalized graphene, nanoparticles, nanowires, nanoribbons, or nanosheets, biological sensing materials such as nucleic acids, aptamers, antibodies, peptides, carbohydrates and others, that are functionalized or not functionalized with labels (molecules or nanoparticles) to promote more than one sensing material property. In one embodiment, the sensing material is an electronic material. In one embodiment, the sensing material is an organic electronic material. In another embodiment, the sensing material is an organic electronic polymer, such as, but not limited to conjugated polymers and intrinsically conducting polymers. In some embodiments, the polymer sensing material is a copolymer sensing material and in other embodiments, the sensing material is a homopolymer sensing material. Some sensing materials include rigid copolymers and other sensing materials include flexible copolymers. Other examples of sensing materials include, but are not limited to, homopolymers and co-polymers of fluorenes, carbazoles, and triarylamines with rigid and flexible links. These classes of polymeric sensing films may be adapted to a given application by designing polymers with the appropriate side chains and end groups.

Organic electronic polymers are sensitive to environmental perturbation because of their electrical transport properties and energy migration. The electrical transport property of organic electronic polymers is a material bulk transport property and as a result, the response of this material property can be more sensitive than potentiometric and amperometric methods that are dependent on local electronic structure. Organic electronic polymers have the ability to amplify response to an analyte binding event. This amplification is due to the efficient energy transfer in organic electronic polymers that allows excitation energy from large areas to be effectively funneled into the analyte binding sites.

Organic electronic polymers, in various embodiments, provide detection of analytes using one or more simultaneous vapor-response mechanisms such as changes in density of charge carriers, changes in mobility of charge carriers, conformational transitions of polymer chain, and polymer swelling. The design of the contributions of these response mechanisms to the overall response of the sensing materials results in the creation of response patterns of various analytes by the synthesized polymers. These and other response mechanisms can be also used for detection of analytes in liquids, where analytes in liquids can be proteins, nucleic acids, viruses, cells, bacteria, spores, toxins.

Multivariate calibration methods offer several advantages over univariate calibration methods. Signal averaging is achieved since more than one measurement channel is employed in the analysis. Also, the concentrations of multiple species may be measured if they are present in the calibration samples. A calibration model is built by using responses from calibration standard samples.

As a nonlimiting example of multivariate analysis, principal components analysis (PCA) can use to extract the desired descriptors from the measured data such as complex impedance spectra data. PCA is a multivariate data analysis tool that projects the data set onto a subspace of lower dimensionality with removed colinearity. PCA achieves this objective by explaining the variance of the data matrix in terms of the weighted sums of the original variables with no significant loss of information. These weighted sums of the original variables are called principal components (PCs). Upon applying the PCA, the data matrix is expressed as a linear combination of orthogonal vectors along the directions of the principal component.

One skilled in the art can apply the PCA analysis to complex impedance spectra collected using a multi-variate sensor (FIG. 7). The resonant complex impedance spectra are first measured using the sensor for three analytes (vapors), followed by conversion to a response pattern of responses to three vapors. For example, individual responses from the sensor with the multivariable signal transduction upon exposure to analyte A1 with its certain concentration C1 are mathematically combined into a response pattern A1C1; individual responses upon exposure to analyte A1 with its other certain concentration C2 are mathematically combined into a response pattern A1C2; or exposures to another analyte A2 with it different concentrations C1 and C2 produce response patterns A2C1 and A2C2. In one embodiment, a sensor with the multivariable signal transduction should have non-overlapping response patterns to different analytes and their concentrations in order to be used to detect different analytes and their different concentrations. The response pattern shows (FIG. 7) results of PCA of three vapors demonstrating good selectivity.

In some embodiments, the synthetic strategy for sensing materials includes the synthesis of homo-polymers and co-polymers based on their monomer composition and their inherent functional groups. Unlike the synthesis of classical sorbing polymers for VOC (volatile organic compound) detection, wherein the composition of monomers and their functional groups can only alter the partition coefficient of the VOC into the polymer film, these types of changes in monomer composition and functional groups for conjugated polymers significantly alter the vapor-response mechanisms. For example, in one embodiment, the presence of several simultaneous vapor-response mechanisms in a single conjugated polymer sensing material is one of the enablers that differentiate some of the sensing materials from classic vapor-sorbing sensing materials employed in many other sensors.

A sorbing polymer for vapor detection is a polymer wherein the composition of monomers and their functional groups can only alter the partition coefficient of the vapor into the polymer film (uptake the vapor by polymer) and does not detectably change density of charge carriers, changes in mobility of charge carriers, polymer protonation, polymer deprotonation.

Organic electronic materials that may be used in the sensor and method embodiments of the present invention have diverse charge transporting properties, energy band-gaps, and high operational stability. In some embodiments, these properties are controlled through chemical synthesis and design by: (1) altering the structure and composition of the pendent functional group "R", (2) preparing blended co-polymers whereby the electronic properties are controlled by the relative ratios of each monomer, and (3) altering the rigidity of the backbone by selecting an appropriate chemistry to link monomers or oligomers together which can ultimately control the polymer's film morphology.

In addition, the effects of the linking chemistry in making polymeric materials with flexible links are important. The linking chemistry of the polymers controls the ability of an analyte to diffuse into the conductive network. In some other embodiments, the permeability of the sensing material to analytes is altered by making the backbone of the polymer more flexible. In various embodiments, the flexible links are based on diphenylpropanes (DPP) and its derivatives. In other embodiments, the addition of fluorene (F) containing substituents to the flexible links of the polymers influences their dielectric constant, stability, selectivity against moisture, and increases the solubility relative to their non fluorinated analogues. Nonlimiting examples of links are DPP, 4F-DPP, 6F-DPP, and 10F-DPP. These molecules provide diversity in sensor response by incorporating fluorene into the flexible segments.

Non-limiting examples of functional groups that are employed with the polymers in the sensing materials of the present invention are presented in Table 1. These functional groups have diverse vapor-interaction abilities that may facilitate sensing efficiency. Using these functional groups, the conjugated co-polymers are tailored to additionally modify the charge-carrying co-polymer network to respond to a particular analyte.

TABLE 1

| Vapor-interaction abilities of functional groups of conjugated polymers. | | | |
| --- | --- | --- | --- |
| Pendant functional group | Available interaction for sensing | Examples of available functional group | Example of sensed analyte |
| Alkyl | van der Waals | alkanes, ethers, tertiary amines | nonpolar aprotic (benzene) |
| Aryl | π-π stacking | electron-rich and electron poor aromatic rings | nonpolar and aromatic (benzene, toluene, chlorinated benzenes) |
| Halogen | Inductive | perfluorinated | fluorinated and halogenated ($CH_2Cl_2$, $CHCl_3$, TCE) |

TABLE 1-continued

Vapor-interaction abilities of functional groups of conjugated polymers.

| Pendant functional group | Available interaction for sensing | Examples of available functional group | Example of sensed analyte |
|---|---|---|---|
| Polar protic | Hydrogen bonding | carboxylic acids, amides, amines, alcohols | polar protic and aprotic (acetonitrile, acetone, ammonia) |
| Polar aprotic | van der Waals, hydrogen bonding | Esters, ethers, tertiary amine | polar protic (MeOH, EtOH, water) |

The following examples provided are not intended to limit the invention, as defined in the appended claims, in any manner.

In each of the examples, resonant sensors were fabricated by coating an antenna structure with a sensing material comprising one or more groups of organic electronic polymers: flexible polymers, rigid co-polymers, and rigid homo-polymers or oligomers. The sensing materials were applied onto the resonant antenna by a conventional draw-coating process. Measurements of the complex impedance of RFID sensors were performed with a network analyzer (Model E5062A, Agilent Technologies, Inc. Santa Clara, CA) under computer control using LabVIEW™. The network analyzer was used to scan the frequencies over the range of interest and to collect the complex impedance response from the RFID sensors. For gas sensing, generation of different concentrations of vapors was done using a computer-controlled vapor-generation system. Collected complex impedance data was analyzed using KaleidaGraph® (Synergy Software, Reading, PA) and PLS_Toolbox 3.5® (Eigenvector Research, Inc., Manson, WA) operated with MATLAB® (The Mathworks Inc., Natick, Mass.).

EXAMPLE 1

As an example, polyaniline (PANI) polymer was selected to create a response pattern of various analytes when PANI is deposited onto the resonant sensor with the multi-variate signal transduction. It is known that the response mechanism of PANI to $NH_3$ involves polymer deprotonation, while the response mechanism to $H_2O$ involves formation of hydrogen bonds and swelling. Results of sensor exposures to $NH_3$ and $H_2O$ vapors are presented in FIG. 8. Deprotonation of the film upon $NH_3$ exposures resulted in the increase in film impedance $Z_p$ and shifts of the sensor resonance $F_p$, $F_1$, and $F_2$ to higher frequencies. The formation of hydrogen bonds and swelling of the polymer upon $H_2O$ exposures resulted in the decrease in $Z_p$ and shifts of $F_p$, $F_1$, and $F_2$ to lower frequencies. Measurements of multiple output parameters from a single sensor revealed different recovery kinetics of responses $Z_p$, $F_1$, $F_2$, and $F_p$ during experiments with $NH_3$. Responses $Z_p$, $F_1$, and $F_p$ showed a partial recovery from $NH_3$, while $F_2$ response was irreversible with only 1.2-3.5% signal recovery.

EXAMPLE 2

A poly(fluorene)-DPP copolymer (PFDPP), a flexible polymer, was used as the sensing material. The structure of the copolymer is given by structure 1 below:

(1)

Figure 9:
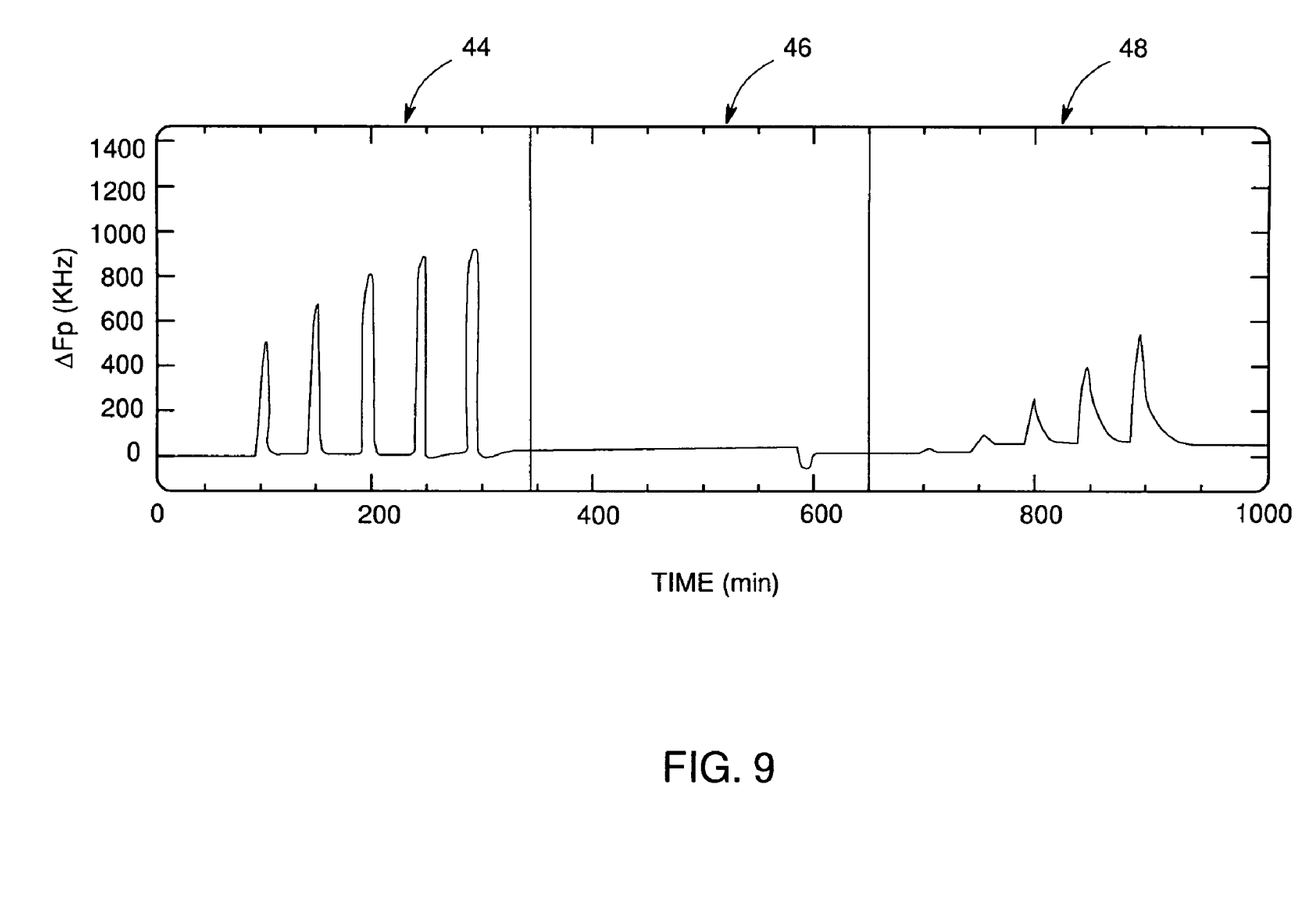
FIG. 9 is a graph showing a sensor response to a change in frequency ($\Delta Fp$) for samples of tetrachloroethane (TCE) (44), water (46) and toluene (48), wherein the sensor material of this example comprises a poly(fluorene)-diphenylpropane conjugated copolymer.

This copolymer was used to test the response for analytes such as trichloroethylene (TCE), toluene and water vapor. FIG. 9 line plots 44, 46, 48 illustrate the variation with time in the observed resonance frequency with the introduction of TCE, toluene and water vapor respectively. The observed response to TCE at the lowest tested concentration of 0.02 P/Po was 20 times stronger than the response to toluene. Furthermore, response to 0.02 P/Po of TCE was about 10 times stronger than response to the highest tested water vapor concentration of 76% RH and the signal response to water was in the opposite direction than to TCE or toluene.

In some embodiments, the conjugated PFDPP copolymer also showed good response stability over several weeks of testing. PFDPP copolymer was also tested for repetitive response to 0.1 P/Po of TCE vapor mixed with a variable-humidity carrier gas over the wide range of humidity from 0 to 76%. In some embodiments, as illustrated by the measurements shown in FIG. 10, the sensing film did not change the response magnitude to TCE even at high humidity. Regions

Figure 10:
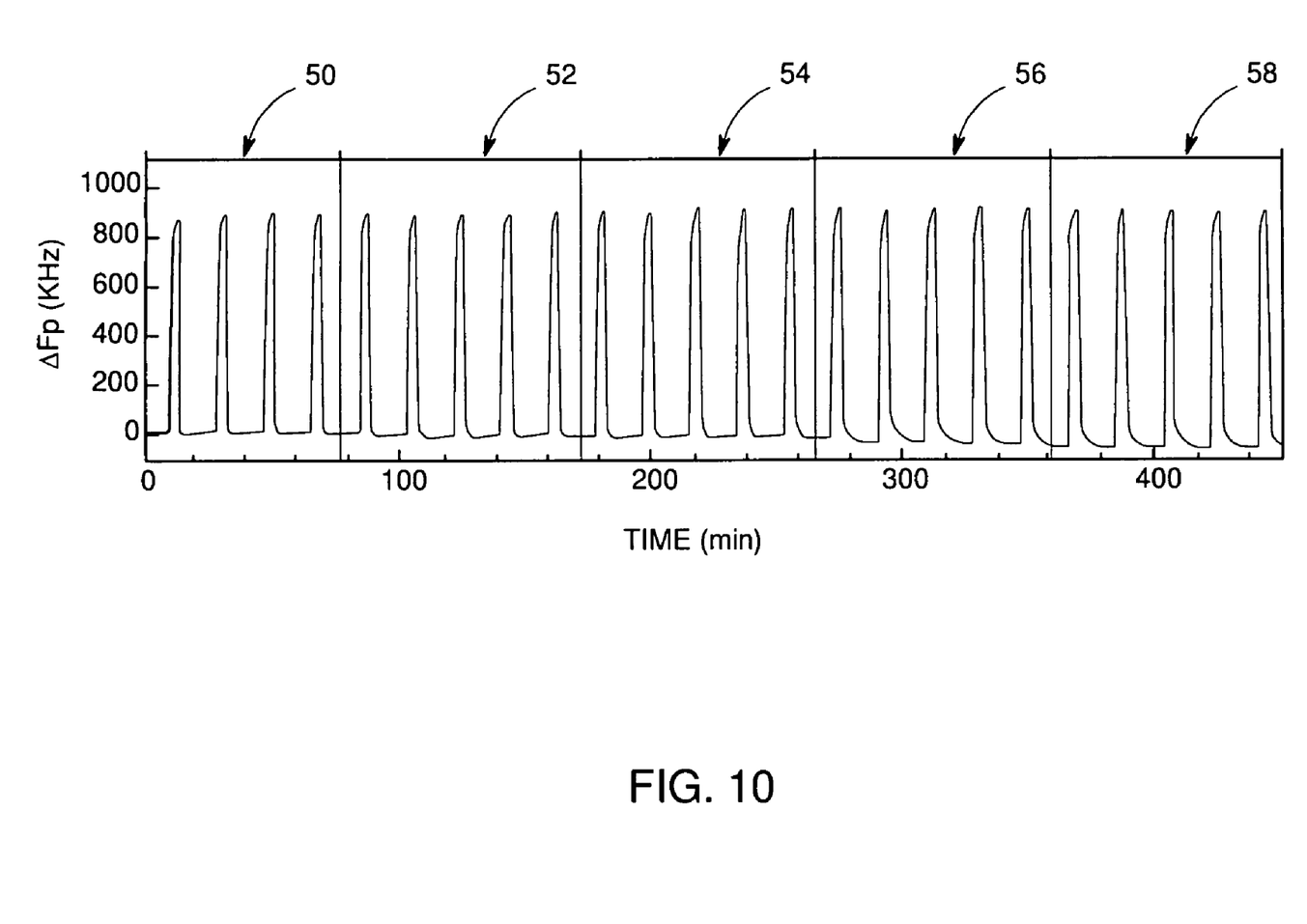
FIG. 10 is a graph showing a sensor response to a change in frequency ($\Delta Fp$) for replicate exposures of a sample of toluene at various humidity levels, 0% RH (50), 22% RH (52), 44% RH (54), 65% RH (56), 76% RH (58) wherein the sensor material of this example comprises a poly (fluorene)-polycarbonate conjugated copolymer. RH is relative humidity.

50, 52, 54, 58, 58 in FIG. 10 correspond to relative humidity (RH) levels of 0, 22, 44, 65, 76% RH respectively. The detection limit (S/N=3) for TCE was calculated to be 1.2 ppm. This detection limit was an improvement of 10 to 20 times over other conventional materials employed with the same RFID antenna structures. The properties of the functional group and the particular chemistry used to link the conductive polymers together determine the VOC response.

EXAMPLE 3

A homo-polymer of triarylamines (PTA), a rigid homopolymer, was used as the sensing material. The structure of the conjugated homopolymer is given by structure 2 below:

(2)

Figure 11A:
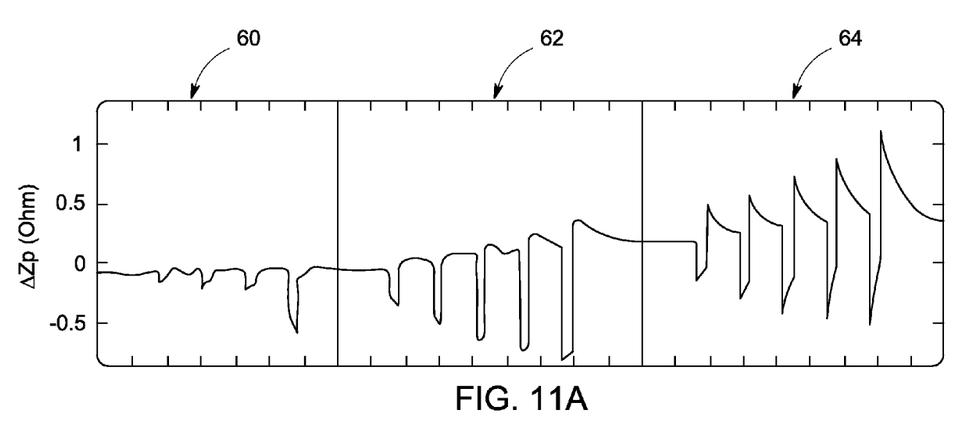
FIG. 11 is a graph illustrating the selectivity of a sensor response to changes in the complex impedance $\Delta Zp$ (A) and frequency $\Delta Fp$ (B) for samples of water (60 and 66 respectively), trichloromethane (62 and 68 respectively) and dichloromethane vapors (64 and 70 respectively), wherein the sensor material comprises a homopolymer of triarylamines.
Figure 11B:
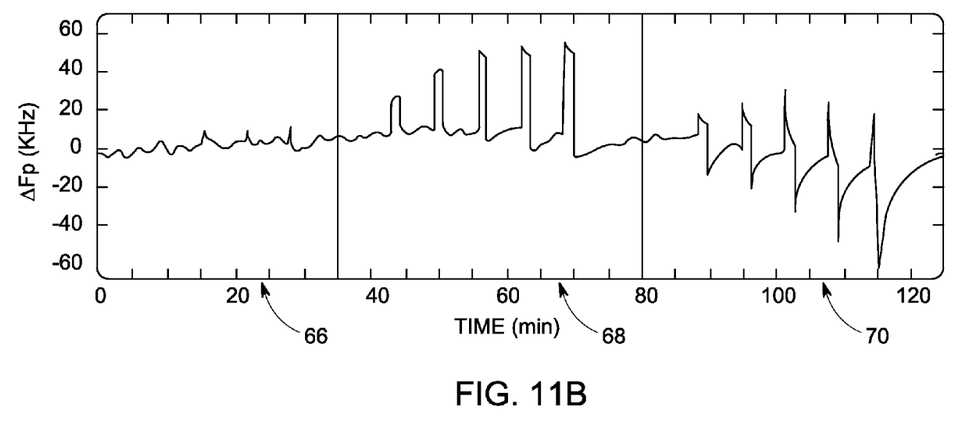

Unlike trichloromethane, the solubility of PTA in dichloromethane was very poor. The selectivity of this polymer was tested in response to trichloromethane and dichloromethane vapors while water vapor was used as an interference (FIG. 11). An examination of the baseline corrected Zp (complex impedance) response for water (line plot 60), trichloromethane (line plot 62) and dichloromethane (line plot 64) shows a signal decrease upon exposure to all tested vapors. The Fp response to water vapor (66) even at 76% RH was almost undetectable, while response to trichloromethane vapor (line plot 68) showed an increase in signal. The response to dichloromethane vapor (line plot 70) showed a decrease in signal.

Other some embodiments describe, several other candidates for the selectivity to trichloromethane/dichloromethane are co-polymers of carbazoles and triarylamines.

EXAMPLE 4

A co-polymer of fluorenes (80%) and triarylamines (20%) (PFT), which is a rigid copolymer, was used as the sensing material. Experiments with a rigid co-polymer were performed with PFT and the structure of PFT is given by structure (3) below.

(3)

Figure 12A:
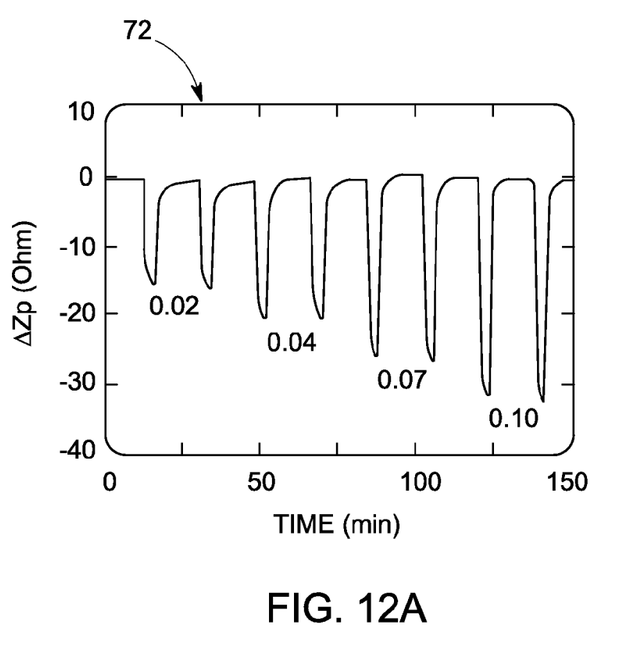
FIG. 12 is a graph illustrating the sensitivity of a sensor response to change in complex impedance $\Delta Zp$ (A) (72) and frequency $\Delta Fp$ (B) (74) for a sample of toluene vapor, wherein the sensing material comprises a copolymer of 80% fluorenes and 20% triarylamines.
Figure 12B:
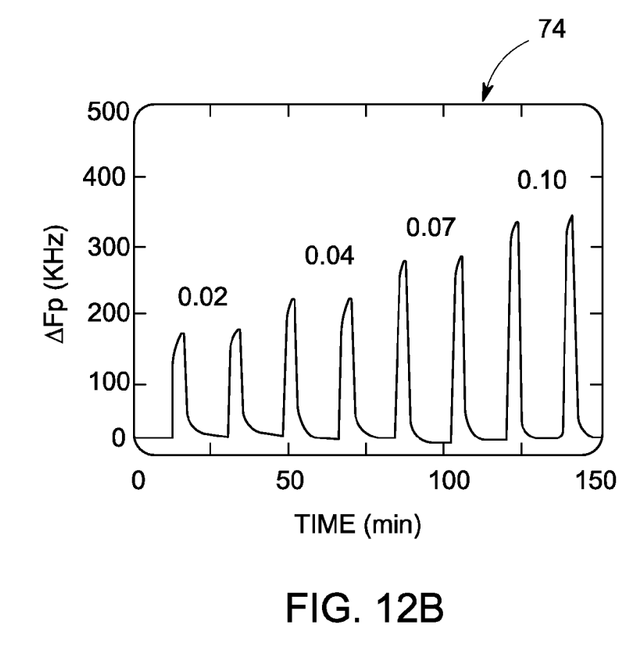

PFT demonstrated a very strong response magnitude to nonpolar vapors such as toluene, benzene, and others. FIG. 12 shows the results (variation in response frequency (line plot 72) and complex impedance (line plot 74)) of replicate exposures of the sensor to variable concentrations of toluene. Initial calculations of the detection limit of toluene (at S/N=3) resulted in a sub-ppm (0.9 ppm) detection limit.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A system for selectively determining at least two analytes, comprising:
   at least one resonant sensor circuit comprising a sensing material that predictably affects a resonant complex impedance response of a sensor electrode, wherein the sensing material comprises at least two material properties that change upon exposure to two or more analytes; and
   a processor that generates a multivariate sensor response pattern that is based at least in part on a change in at least two of the material properties of the sensing material to determine a characteristic of the at least two analytes.

2. The system of claim 1, wherein a ratio of change of the at least two material properties varies for different analyte compositions, different analyte concentrations or both.

3. The system of claim 1, wherein the multi-variate sensor response pattern identifiably separates patterns associated with different analytes varying in composition or concentration.

4. The system of claim 1, wherein the at least one resonant sensor circuit predictably affects the resonant complex impedance response in the presence of at least one analyte and one interference.

5. The system of claim 1, wherein the resonant complex impedance response of the at least one resonant sensor circuit is measurably altered on variation of one or more dielectric properties of the sensing material.

6. The system of claim 1, wherein the sensing material comprises an organic electronic material.

7. The system of claim 1, wherein the sensing material comprises polyaniline (PANI), poly(fluorene)-diphenylpropanes copolymer (PFDPP), polymer of triarylamines (PTA), polymer of fluorenes and triarylamines (PFT) and combinations thereof.

8. The system of claim 1, wherein the sensing material comprises a nanotube, nanoparticle, or nanosheet.

9. The system of claim 1, wherein the sensing material comprises a carbon nanotube or graphene sheet.

10. The system of claim 1, wherein the change in the at least two material properties is at least partially caused by an analyte response mechanism, wherein the mechanism is selected from a group consisting of, changes in density of charge carriers, changes in mobility of charge carriers, conformational transitions of polymer chain, polymer swelling, and combinations thereof.

11. The system of claim 1, wherein the analyte is selected from a group consisting of, volatile organic compounds, oxidizing and reducing gases, dissolved gases, biological species in water and combinations thereof.

12. The system of claim 1, wherein the resonant complex impedance response is operably consistent in the presence of varying levels of humidity.

13. The system of claim 1, wherein the resonant complex impedance response of the at least one sensor circuit changes relative to a concentration of analyte.

14. The system of claim 1, wherein the system operates within an electro magnetic spectrum comprising a frequency range from about $10^5$ Hertz to $10^{15}$ Hertz.

15. A system for selectively determining at least two analytes, comprising:
    at least one resonant sensor circuit comprising a sensing material that predictably affects the resonant complex impedance response of a sensor electrode, wherein the sensor electrode comprises an inductor-capacitor-resistor circuit and wherein the sensing material comprises at least two material properties that change upon exposure to two or more analytes; and
    a processor that generates a multivariate sensor response pattern that is based at least in part on a change in at least two of the material properties of the sensing material to determine a characteristic of at least two of the analytes.

16. The system of claim 15, wherein the inductor-capacitor-resistor circuit comprises a combination of parallel and series capacitance elements.

17. The system of claim 15, wherein the system operates within an electro magnetic spectrum comprising a frequency range from about $10^5$ Hertz to $10^{15}$ Hertz.

18. A sensing device adapted to detect at least two analytes, comprising:
    a resonant sensor circuit comprising a sensor electrode and a sensing material disposed on the sensor electrode, wherein the sensing material has at least two material properties that change upon exposure to two or more analytes;
    a processor that generates a multivariate sensor response pattern that is based at least in part on a change in at least two of the material properties of the sensing material to determine a characteristic of at least two of the analytes; and
    a memory chip to store user-defined digital data comprising the multivariate sensor response pattern.

19. The sensing device of claim 18, wherein the digital data comprises calibration parameters of the resonance sensor circuit.

20. The sensing device of claim 18, wherein the resonant sensor circuit comprises one or more of an antenna, a capacitor, or an integrated circuit memory chip.

21. The sensing device of claim 18, where in the resonant sensor circuit is an optical circuit.

22. A method for selectively detecting at least two or more analytes in presence of an interference, comprising:
    contacting a sensor with an at least two of the analytes to generate multiple response signals that are not substantially correlated with each other; wherein the sensor comprises at least one resonant sensor circuit comprising a sensing material which comprises at least two material properties that change in the presence of at least two of the analytes; and
    generating a multi-variate sensor response pattern from the multiple response signals in the presence of the interference to detect a characteristic of the at least two or more analytes.

23. The method of claim 22, further comprising acquiring the complex impedance response of the sensor.

24. The method of claim 22, wherein determining the multi-variate sensor response pattern comprises performing a multi-variate analysis on a complex impedance response of the sensor.

25. The method of claim 22, wherein the multi-variate sensor response pattern identifiably separates patterns associated with different analytes varying in composition or concentration.

* * * * *